Figure 1:
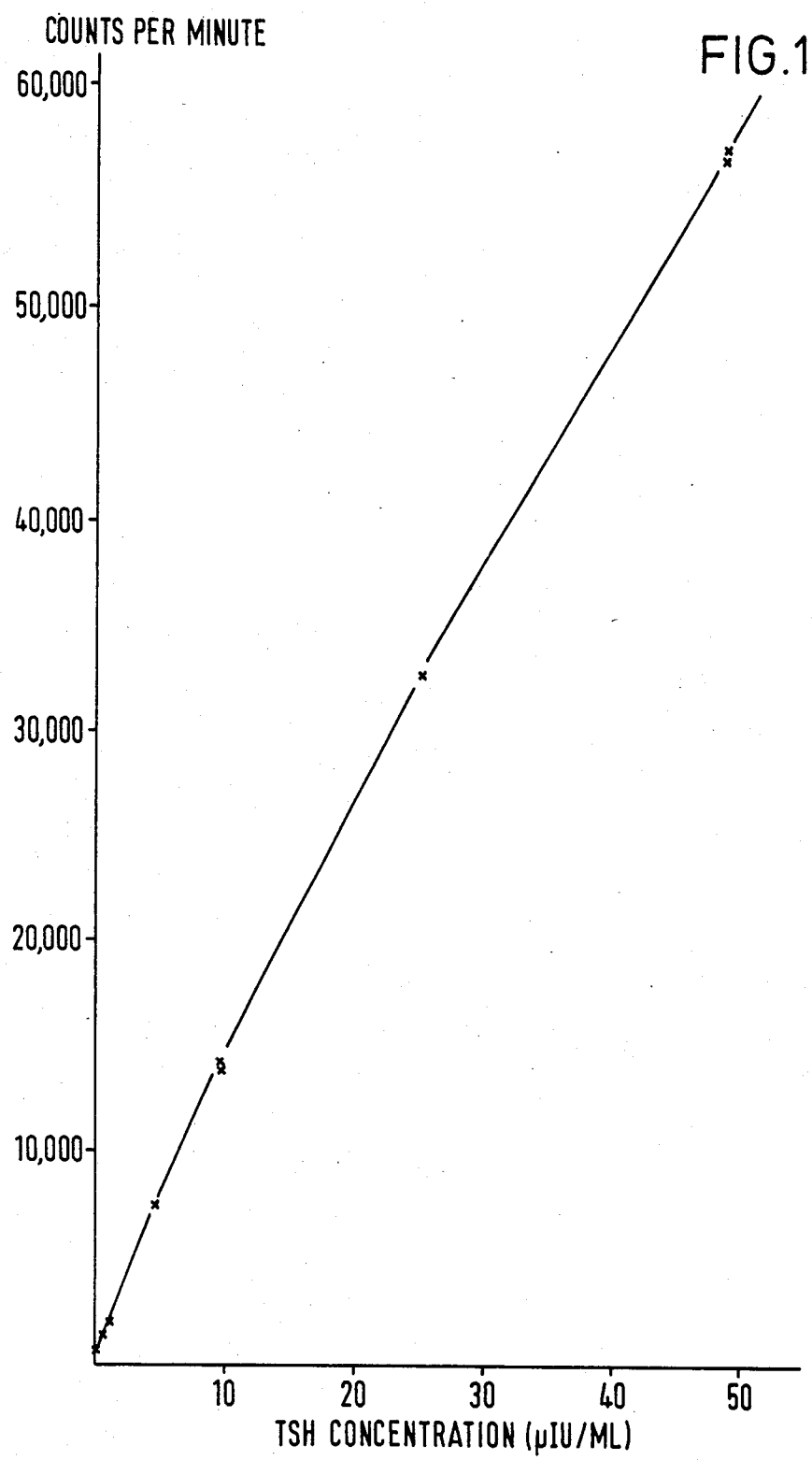

United States Patent [19]

Forrest et al.

[11] Patent Number: 4,659,678

[45] Date of Patent: Apr. 21, 1987

[54] IMMUNOASSAY OF ANTIGENS

[75] Inventors: Gordon C. Forrest, Ingatestone; Philip R. P. Salacinski, Stratford; Kenneth Siddle, Lode, all of England

[73] Assignee: Serono Diagnostics Limited, Great Britain

[21] Appl. No.: 535,882

[22] Filed: Sep. 26, 1983

[30] Foreign Application Priority Data

Sep. 29, 1982 [GB] United Kingdom ............... 8227826

[51] Int. Cl.$^4$ ............... G01N 33/563; G01N 33/53; G01N 33/577; B65D 69/00
[52] U.S. Cl. ............................ 436/512; 436/513; 436/518; 436/531; 436/548; 436/800; 436/808; 436/819; 436/822; 436/828
[58] Field of Search ............... 436/512, 513, 518, 548, 436/500, 510, 531, 800, 804, 808, 810, 817, 828; 435/7; 422/61

[56] References Cited

U.S. PATENT DOCUMENTS

| | | | |
|---|---|---|---|
| 4,185,084 | 1/1980 | Mochida et al. | 436/518 |
| 4,243,749 | 1/1981 | Sadeh et al. | 436/531 |
| 4,273,756 | 6/1981 | Ling et al. | 436/513 |
| 4,347,311 | 8/1982 | Schmitz | 436/518 |
| 4,376,110 | 3/1983 | David et al. | 436/542 |
| 4,410,633 | 10/1983 | Hertz et al. | 436/531 |
| 4,433,059 | 2/1984 | Chang et al. | 436/512 |
| 4,444,878 | 4/1984 | Paulus | 436/512 |
| 4,459,360 | 7/1984 | Marinkovich | 436/530 |
| 4,471,058 | 9/1984 | Smith et al. | 436/529 |
| 4,474,892 | 10/1984 | Murad et al. | 436/513 |
| 4,477,577 | 10/1984 | Nakamura et al. | 436/510 |
| 4,481,298 | 11/1984 | Cone, Jr. et al. | 436/512 |
| 4,490,473 | 12/1984 | Brunhouse | 436/531 |

OTHER PUBLICATIONS

Sevier et al., Clin. Chem., 27 (1981) 1797–1806.
Ey et al., Immuno Chemistry, 15 (1978) 429–36.

Primary Examiner—Christine M. Nucker
Attorney, Agent, or Firm—Ostrolenk, Faber Gerb & Soffen

[57] ABSTRACT

A method of immunoassay of an antigen in a liquid sample wherein a complex is formed between antigen contained in the said sample and two or more antibody reagents, and the said complex is bound to a solid support by non-covalent bonding as defined herein; and the amount of complex becoming bound to the support is determined; the process employing at least one monoclonal antibody reagent. Labelling methods including radio-active, fluorimetric and enzyme labelling may be used to effect determination of the binding of the complex to the solid support. The solid support may take the form of particles, beads, wall-coatings on the reaction vessel or an insert of large surface area. The method is particularly applicable to the assay of TSH, CEA, HCG, alphafeto protein, immunoglobulins, viruses, allergens, bacteria, toxins, drugs and vitamins. Use of monoclonal reagents improves the specificity of the process, and also decreases non-specific binding.

9 Claims, 3 Drawing Figures

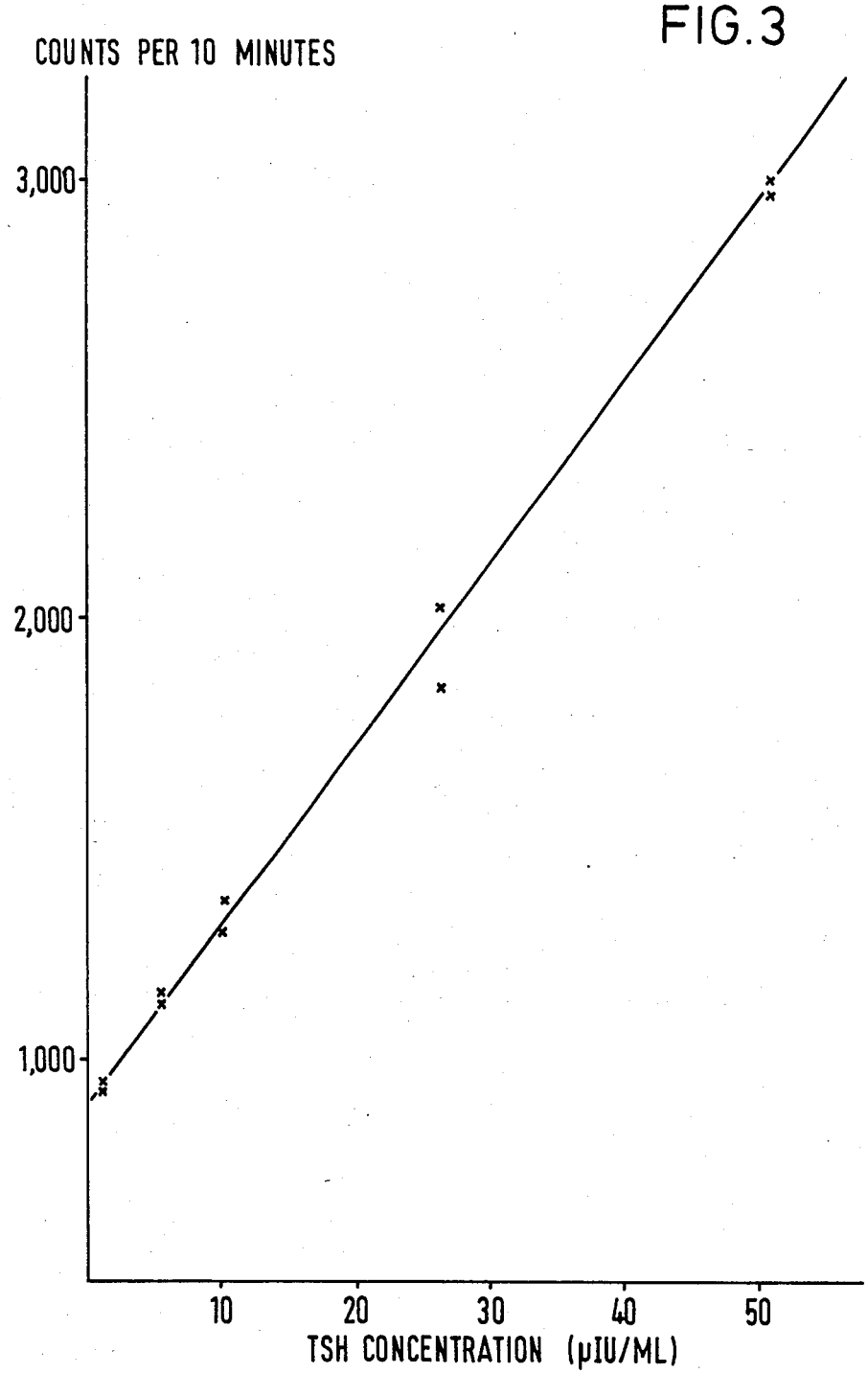

IMMUNOASSAY OF ANTIGENS

The present invention relates to methods of immunoassay of antigens, and to kits for carrying out such methods.

In this specification, the term "antiqen" is to be taken to include any substance to which antibodies can be produced, and accordingly includes within its scope haptens, which may have been rendered antigenic for the purpose of producing antibodies.

Immunoassay techniques rely upon the formation of a complex between the antigen being assayed and antibodies which are added as part of the immunoassay procedure. Means are provided whereby the amount of antigen:antibody complex formation is detectable.

There are several known methods of immunoassay employing antibodies which are labelled so as to be analytically identifiable. "Sandwich" or "two-site" techniques involve the formation of a complex between the antigen and two antibodies. A convenient method of detecting complex formation in such techniques is to provide that one antibody is labelled and the unlabelled antibody is bound to a solid phase support so that the complex can readily be isolated. Where a radioactive label is employed this technique is known as immunoradiometric assay (IRMA). An example of such an assay is that for thyroid stimulating hormone (TSH) in human serum, in which the serum is mixed with $^{125}I$-labelled sheep anti-TSH antibodies, and with sheep anti-TSH antibodies coupled to a solid phase (e.g. particles). The TSH binds to both antibodies, and by measuring the amount of label remaining in solution or becoming bound to the soiid phase (via TSH), the amount of TSH can be determined.

One difficulty with this type of assay is to produce sufficiently pure labelled antibody: whilst this can be done, it is a laborious procedure and hence relatively expensive. Recently, this problem has been reduced by the availability of monoclonal antibodies (as opposed to the polyclonal antibodies previously used). Pure labelled monoclonal antibodies can be made relatively easily, and as a result there has been renewed interest in the above type of technique.

It is a feature of the technique described above that a significant incubation period is normally required to ensure that the reaction goes (so far as is possible) to completion, and this is due at least in part to the fact that the antigen in solution is required to react with antibody bound to a solid phase. With a view to reducing the incubation time, it has been proposed to modify the procedure. A labelled antibody in solution is used (as before) but together with another antibody (towards the antigen) in solution. The antibody coupled to the solid phase is, in this modification, a second antibody generated against the other (non-labelled) antibody. Thus, the labelled antibody and the other antibody in solution bind to the antigen under assay. The insolubilised second antibody binds to the other antibody (and thus to any antigen and labelled antibody bound thereto). The advantage of this modification is that the liquid phase reaction (between the antigen, the labelled antibody and the other antibody) occurs rapidly, and the reaction with the insolubilised second antibody also occurs relatively quickly, thus providing a faster overall time for the assay.

In both the classic technique and the modified procedure described, the sensitivity of the assay is critically dependent on the amount of non-specific binding which occurs. The more non-specific binding there is, the less sensitive is the assay. One of the most important causes of non-specific binding is the solid phase itself which can, for example, sometimes bind directly to labelled antibody. Additionally, the solid phase may entrap a volume of sample containing free label. Both effects contribute to the problem of non-specific binding. The extent of such non-specific binding can be reduced by keeping the amount of solid phase to a minimum, but this in turn results in a reduction in the overall speed of the assay reaction because the speed is proportional to the amount of solid phase present.

We have now devised modified techniques in which significant improvements may result from the use of monoclonal antibodies. The techniques for making monoclonal antibodies are well known (see, for example, Galfre, G. & Milstein, C. (1981) "Preparation of Monoclonal Antibodies: Strategies and Procedures" Methods in Enzymology 73, 1-46), and will not be further described herein.

In the following portion of this specification, the term "antibody reagent", unless context dictates otherwise, is to be taken to include reference to intact antibodies and to fragments thereof. The term "fragment", as used herein, unless qualified so as to indicate otherwise, is to be taken to refer to fragments which contain the binding region of the antibody. Such fragments may be Fab-type fragments which are defined as fragments devoid of the Fc portion, e.g. Fab, Fab' and F(ab')$_2$ fragments, or may be so-called "half-molecule" fragments obtained by reductive cleavage of the disulphide bonds connecting the heavy chain components in the intact antibody. The use of monovalent fragments, e.g. Fab, Fab' and half-molecule fragments, is preferred.

The method of preparation of fragments of antibodies is well known in the art and will not be described further herein. The antibody reagents employed in the invention may be derived from any of the various subclasses of immunoglobulins including in particular IgG and IgM and may be raised in any of the animal species commonly used for this general purpose, e.g. sheep, goats, mice.

The present invention relates to a method of immunoassay of an antigen in a liquid sample wherein a complex is formed between antigen contained in the said sample and two or more antibody reagents, and the said complex is bound to a solid support by non-covalent bonding, as defined herein; and the amount of complex becoming bound to the support is determined; the process employing at least one monoclonal antibody reagent.

By the term "non-covalent bonding" as used herein is meant immunological bonding as in an antibody: antigen or antibody: hapten bond or non-immunological bonding such as that between a specific binding protein and its ligand e.g. in the reaction of protein A and the Fc portion of an antibody or the binding between substances such as avidin and biotin.

Figure 2:
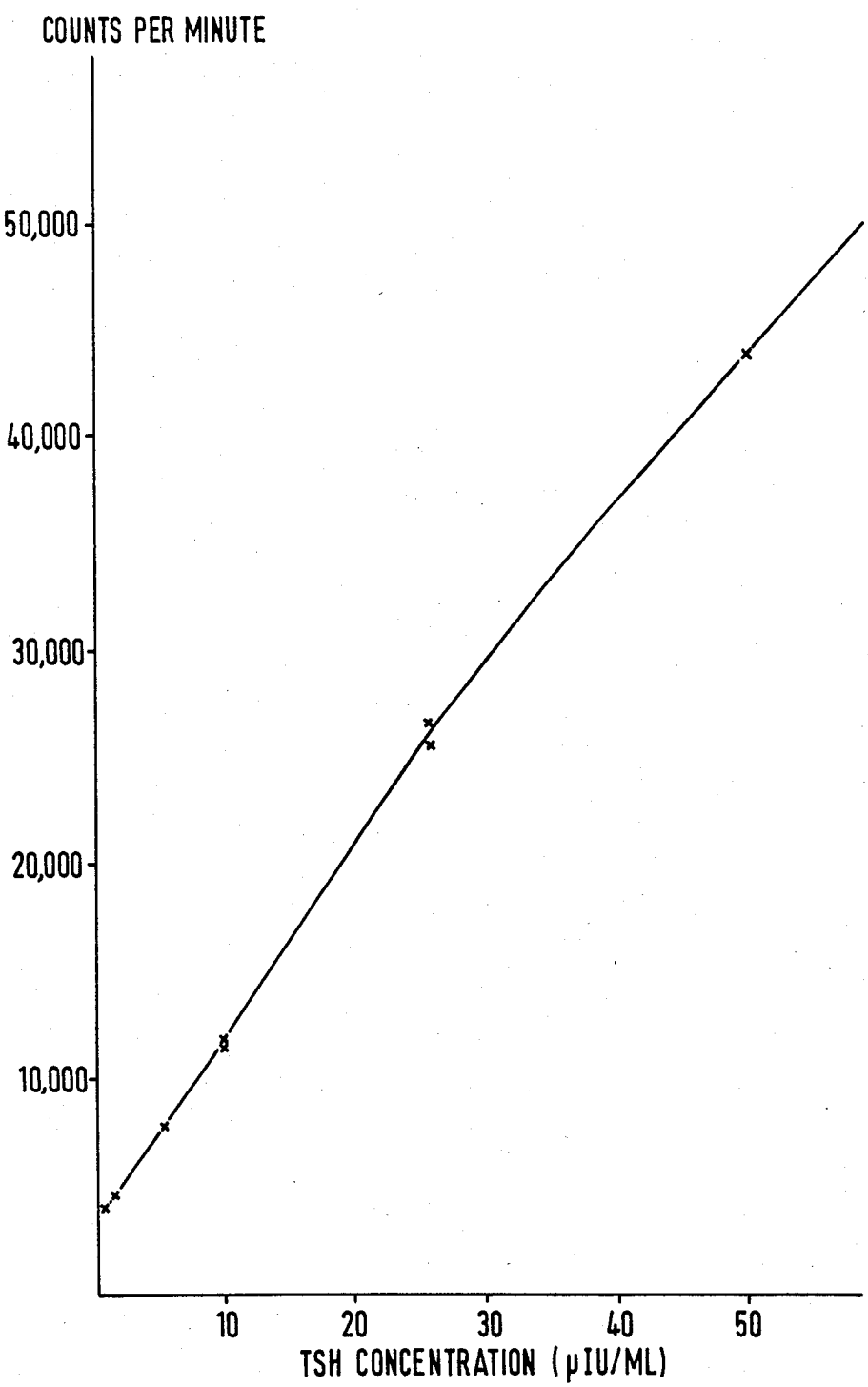

FIGS. 1, 2 and 3 are dose response curves of the TSH assay of examples 1, 2 and 3, respectively.

At least one antibody reagent employed in the method of the invention must be monoclonal, and it will generally be advantageous for the other antibody reagent(s) also to be monoclonal. It may also be advantageous for the antibody reagents to be employed in the form of fragments. Preferably the antibody reagents will be selected so as to be directed against different, roomly-spaced, determinants of the antigen.

In a preferred aspect, the invention relates to methods of immunoassay employing the "sandwich" technique in which one of the antibody reagents complexing with the antigen is labelled.

Accordingly, a preferred aspect the invention provides a method of immunoassay of an antigen in a liquid sample which comprises incubating a mixture of:
(a) the liquid sample;
(b) labelled antibodies to the antigen under assay;
(c) a reagent comprising antibodies to the antigen under assay;
(d) a reagent capable of binding to component(c) by non-covalent bonding as defined herein, but which is not directly bindable to either component (a) or component (b), the said reagent
(d) being bound to a solid phase support, at least one of components (b), (c) and (d) comprising monoclonal antibodies; separating the solids fraction from the liquid fraction, determining the amount of label in one of the said fractions and, therefrom, the amount of antigen present in the sample. As stated above, one or more of the antibody reagents may be employed in the form of fragments.

The component (b) may be labelled with an analytically indicatable atom or group such as a radioactive atom or group e.g. $^{125}I$, or other methods of labelling known in the art may be used, e.g. fluorimetric labelling or enzyme labelling, which may be direct or indirect, covalent or non-covalent.

The solid support may take the form of finely divided inert particles or beads (e.g. latex particles) and such particles or beads may if desired be magnetic or magnetisable to facilitate the phase separation step. The term "magnetic" as used herein shall be taken to include within its scope ferromagnetic, paramagnetic and superparamagnetic substances. The term "magnetisable" shall be construed accordingly. Suitable magnetic or magnetisable solid supports are described in "Immunoassays for Clinical Chemistry" (Ed. Hunter and Corrie, Churchill Livingstone, Edinburgh (1983)) pp. 147-162; for example, particles of cellulose composite containing $Fe_3O_4$ may be used. In general, any material which facilitates magnetic separation may be employed in the solid support.

Alternatively, the solid support may comprise a generally rod-shaped multi-finned insert. It is important that the surface area of the solid support should be as large as possible. Instead of using particles, beads or inserts, the solid phase may comprise a coating on the wall of the reaction vessel (e.g. test tube) or on the wall of a tube through which the reaction mixture passes or in which it is incubated. The phase separation step then consists simply in removing the liquid from contact with the coating. The techniques of binding the component (d) to suitable supports are well known. Selective binding of component (c) to component (d) may be accomplished by various methods. Thus, component (d) may comprise an antibody raised to reagent (c) and bound to the solid phase support by conventional means. Selective binding of the antibody reagent of component (d) to reagent (c) may be accomplished by the antibody reagents of components (b) and (c) comprising monoclomial antibodies of different animal species, such that the solid phase antibody reagent of component (d) will bind directly to reagent (c), but not to reagent (b).

Thus for example, there is provided a method of immunoassay of an antigen in a liquid sample, which comprises incubating a mixture of:
(a) the liquid sample;
(b) labelled antibodies to the antigen of a first animal species;
(c) first antibodies to the antigen of in a second animal species; and
(d) second antibodies capable of binding specifically to said first antibodies; said second antibodies being bound to an insoluble support; and the antibodies of at least components (b) and (c) being monoclonal; separating the solids fraction from the liquid fraction of the mixture, and determining the amount of label in one of said fractions and, therefrom, the amount of antigen present in the sample.

Alternatively, if components (b) and (c) are of a different antibody class or sub-class, and reagent (d) has the appropriate class or sub-class specificity, selective binding may be possible even if components (b) and (c) comprise antibody reagents raised in the same species.

Preferably, the labelled antibody reagent (b) and the antibody reagent of component (c) are directed against different, roomly-spaced determinants of the antigen.

A further method of selective binding of component (c) to component (d) comprises providing that the labelled component (b) is in the form of Fab-type fragments, and component (c) comprises intact antibodies or half-molecule fragments, these being raised in the same animal species (e.g. the mouse) as the fragments of component (b). In this case, the reagent (d) comprises an antibody reagent, raised in a different animal species, to the Fc part of reagent (c).

Alternatively, Protein A may be used as component (d) in this case since this will bind with the Fc portion of component (c) but not with the Fab-type fragments of component (b).

A further method of binding of component (c) to the solid phase support comprises providing component (c) as a complex of antibody reagents with dual specificity for the antigen and for the solid phase support. Thus, reagent (c) may comprise two different antibody reagents in cross-linked or hybridized form such that one of the said antibody reagents selectively binds to the antigen, and the other selectively binds to reagent (d) which may in this case be another antibody reagent, or may be a hapten. An advantage of using a hapten is that it allows the production of a very high capacity solid phase. It is preferred that both sets of antibody reagents of component (c) should be monoclonal since this improves the efficiency of the cross-linking or hybridisation reaction, and it is to be understood that reagent (c) is a single unitary complex and not a mere admixture of the two said antibody reagents.

As a further method of binding, component (d) may comprise a reagent Y which selectively interacts with a reagent Z provided on reagent (c). The reagent Z may for example be such as to render reagent (c) antigenic to reagent Y which in that case is an antibody reagent raised to reagent Z.

In a preferred embodiment, reagent Z will be a hapten, but antigenic substances such as, for example, proteins, cells, virus particles or membranes may also be employed.

Thus, for example, reagent (c) may be an antibody to the antigen under assay, conjugated with reagent Z (which may be, for example, fluorescein isothiocyanate (FITC), rhodamine isosthiocyanate, 2,4-dinitrofluorobenzene, phenyl isothiocyanate or dansyl chloride). When reagent Z is FITC, reagent Y in that case may be anti-FITC antibody covalently linked to the solid support. The antiserum Y, which is an antibody reagent raised to reagent Z, may be prepared in conventional manner, for example by immunising sheep with FITC conjugated to keyhole limpet haemocyanin. Coupling of the antiserum Y to the solid support may be affected for example using the method of Axen et al (Nature 214, 1302–1304 (1967). Reagent (c) may for example be prepared by direct reaction of reagent Z with antibody, followed by gel filtration, or reagent (c) may be prepared by linking reagent Z indirectly to the antibody using bifunctional reagents or spacer groups. Reagents Y and Z may also for example be a specific binding protein and the corresponding ligand such as for example avidin and biotin which constitute a very rapid, high affinity binding system. The use of such methods of binding offers the great advantage that the reaction can be made very rapid and complete.

It is possible, in certain circumstances, to introduce reagent Z into reagent (c) at multiple sites, thus enhancing its reactivity with the solid phase.

The method of the present invention may be carried out using any of the techniques employed for assays of the "sandwich" type, including the forward, fast forward, reverse and simultaneous techniques.

Preferably, the antigen is complexed with the soluble antibody reagents prior to the addition of the solid phase component. The labelled and unlabelled antibody reagents may be added in any order, or simultaneously, especially where the antibody reagents are directed against different, roomly-spaced determinants of the antigen.

A variation of the "sandwich" technique described above employs two labelled antibody reagents, e.g. one carrying a fluorescing chromophore and the other carrying a chromophore which absorbs light emitted by the fluorescing chromophore. Formation of a sandwich of the two types of antibody reagents with the antigen to be assayed may cause quenching of the fluorescence and the degree of quenching can be used as a measure of the amount of antigen in the sample. In this technique, either one of the antibody reagents, bearing either the fluorescing or the quenching chromophore, may become bound to the solid support.

Detection of compled formation is also possible by binding one or more of the antibody reagents to an enzyme. The other antibody reagent may be bound to a substance which undergoes a chemical change catalysed by the enzyme, or may itself be an enzyme, the formation of the complex with the antigen bringing the enzyme and substance, or the two enzymes, into close proximity producing effects which can be determined.

Thus, an enzyme bound to a first antibody reagent may catalyse a reaction in a substance attached to the other antibody reagent or the two enzymes may catalyse sequential reactions which are interdependent in that the first produces a material essential to the second. Alternatively, the product of the first enzymatic reaction can be an allosteric activator or inhibitor of the second reaction.

The formation of the complex in such methods may be detected using standard techniques such as colorimetry, fluorimetry, luminescence or spectro- photometry.

In a further aspect the invention provides kits of reagents for carrying out the assays of the invention. Thus, for example, a kit according to the present invention may comprise (i) particles or beads carrying the bound reagent (d), (ii) labelled reagent (b), (iii) reagent (c) and (iv) calibrated reference solutions.

The method of the invention has a number of significant advantages over known methods. Where component (d) comprises monoclonal antibodies, a very high capacity solid phase can be produced. As is known, polyclonal antibody normally contains only a small fraction of the specific antibo.dy which is in fact required. As a result, a relatively large amount of polyclonal antibody has been needed in the prior techniques to provide the necessary quantity of specific antibody. By using monoclonal antibody, which is essentially the specific antibody in pure form, far less antibody is needed. In this way, far less solid phase is needed which, in turn, reduces the amount of non-specific binding due to the solid phase. At the same time, the amount of specific antibody is high so that the activity of the bound antibody is not reduced, and the overall reaction rate is not lowered. In this way, the dilemma in the previously described prior art techniques is overcome: the amount of solid phase is reduced (and with it, the non-specific binding attributable thereto) without reducing the activity of the second antibody.

A further advantage associated with the use of the high capacity solid phase made possible by the present invention is in reducing the so-called "high dose hook effect", which can result in spurious results at hiqh antigen concentrations. The point at which the "hook" occurs is determined by the capacity of the solid phase. In the present invention the "hook" can be kept out of the range normally of interest.

The use of monoclonal reagents for the antibody reagents complexing with the antigen improves the specificity of the process, and also decreases non-specific binding.

Whilst the method of the invention has very broad applicability, it is particularly useful in assaying the following antigens, namely: hormones, including peptide (e.g. thyroid stimulating hormone (TSH)) or non-peptide (e.g. steroid and thyroid) hormones; proteins, such as for example tumour markers, e.g. carcinoembryonic ,antigen (CEA),'human chorionic gonadotrophin (HCG), alphafetoprotein; and immunoglobulins, e.g. IgE; viruses, e.g. hepatitis A, hepatitis B and non-A and non-B, allergens, bacteria, toxins, drugs and vitamins.

In the various aspects of the invention, it is possible to use mixtures of antibody reagents, especially for the labelled component, since this increases the specific activity of the antibody-antigenantibody complex, and tends to counteract potential competition between polyclonal and monoclonal antibodies (see Example 1).

In the various aspects of the invention, fragments may be used instead of intact antibodies where this is feasible. The advantages associated with the use of fragments in the methods of the invention instead of intact antibodies are as follows.

A reduction of non-specific binding; i.e. binding between labelled component and a site (e.g. the solid phase support) other than the antigen being assayed is still further reduced by the use of fragments as the labelled component.

The speed of the assay is increased by the use of fragments which are smaller than intact antibody molecules. The smaller size produces faster reaction with the antigen being assayed.

Monovalent fragments, in contrast to intact antibodies which are bivalent, cannot form aggregates e.g.

dimers or more extensive complexes with the antigen. The formation of such aggregates is undesirable in that it may interfere with binding of the complex to the solid phase support.

If, as is generally the case in "sandwich" techniques, the labelled component is used in excess, only one of the valencies of an intact antibody will generally be saturated. This means that one valency is unemployed which reduces the efficiency of the technique.

At high antigen levels, it is possible for two antigens to bind to a single intact antibody which is subsequently detected as a single complex. This will reduce the sensitivity of the technique. The use of monovalent fragments eliminates this effect.

The Fc fragment of the antibody is associated with the activation of the complement system and rheumatoid factor (RF) binding. It is possible that intact antibodies attached to antigen in solution could be complexed by RF present in serum with the result that subsequent complex detection could be inhibited, e.g. by the RF binding interfering with binding to the solid phase support. The use of Fab type fragments (eg. Fab, Fab' or F(ab')$_2$ which do not contain the Fc region) would avoid this effect.

In processes in which the labelled component reacts first with the antigen, the use of labelled fragments will result in a smaller complex, which will make binding to the solid phase support easier. The use of fragments for the solid phase antibody will also make possible the production of a very high capacity solid phase—even higher than where monoclonal intact antibodies are used. The use of the smallest possible labelled fragments will also facilitate the use of more than one labelled entity since steric effects will be significantly reduced. The same considerations will hold when fragments are employed as reagent (c) in the procedures cited.

The following non-limiting examples are intended to illustrate the present invention.

EXAMPLE 1

Assay of TSH

In this assay, selective binding of the reagent (c) to the bound reagent (d) was achieved by interaction of FITC conjugated and bound anti-FITC antibodies. Two $^{125}$I-labelled antibody reagents were employed.

Preparation of the starting materials (i) Combined reagent comprising $^{125}$I-labelled monoclonal antibodies (two types) and FITC conjugated monoclonal antibody.

Monoclonal antibodies were obtained from mouse ascites fluid by the process reported by Milstein and Kohler in Nature 256 495–497 (1975). Antibodies from individual hybridoma cell lines were screened to identify those producing antibody to discrete antigenic determinants. Those having the highest affinities to TSH were selected for use in the assay. Two antibodies were selected for labelling with $^{125}$I and one for conjugation with FITC. Each of those selected exhibited an affinity for TSH of greater than $1 \times 10^{10}$ litres/mole and did not interfere with the other's binding to TSH.

Monoclonal antibodies were labelled with $^{125}$I using the procedure of Hunter et al, J. Immunol. Methods 50, 133–144 (1982), and purified by gel filtration on Sephacryl S-300, giving a product with an average of approximately 1 atom of $^{125}$I per antibody molecule.

Conjugation of FITC to monoclonal antibody was achieved by reacting 200 μg fluorescein isothiocyanate (FITC), Sigma London Chemical Co., England, with 5 mg antibody in 1.4 ml sodium bicarbonate buffer, 0.2 M, pH 9.0, for 18 hours at room temperature. The reaction mixture was purified by gel filtration on Sephadex G-50 superfine, giving a product incorporating an average of 6 molecules FITC per antibody molecule.

The $^{125}$I-labelled monoclonal antibodies and FITC conjugated monoclonal antibody were combined in a single reagent containing approximately $2 \times 10^6$ counts per minute per ml $^{125}$I-labelled antibodies and 2.5 μg/ml FITC conjugated antibody, in a buffer system of 0.05M sodium phosphate, pH 7.4 containing 0.5% (w/v) bovine serum albumin, 0.2% (v/v) normal (non-immune) sheep serum and 0.2% (w/v) sodium azide.

(ii) Solid phase reagent comprising anti-FITC polyclonal antibody covalently linked to magnetisable cellulose particles Anti-FITC was a conventional polyclonal antiserum obtained by immunising sheep with FITC conjugated to keyhole limpet haemocyanin. The magnetisable cellulose particles were a composite of cellulose containing approximately 50% black ferric(ous) oxide ($Fe_3O_4$), with mean particle diameter of 3 micron (see Forrest and Rattle, "Magnetic Particle Radio immunoassay", in Immunoasays for Clinical Chemistry, p. 147–162, Ed. Hunter and Corrie, Churchill Livingstone, Edinburgh (1983)). Anti-FITC antiserum was covalently coupled to the magnetisable cellulose following cyanogen bromide activation of the cellulose, according to the procedure of Axen et al, Nature 214, 1302–1304 (1967). The antiserum was coupled at a ratio of 2 ml antiserum to 1 gram of magnetisable solid phase.

Anti-FITC magnetisable solid phase was diluted to a concentration of 6–8 mg/ml in sodium phosphate buffer 0.05M, pH 7.4 containing 0.25% (w/v) bovine serum albumin, 0.25% (v/v) Triton X-100, 0.8% (w/v) hydroxypropyl methyl cellulose and 0.1% (w/v) sodium azide.

Determination of TSH

Solutions of TSH in normal human serum, calibrated against the 1st International Reference Preparation of human TSH for immunoassay (68/38), were used as standards.

Duplicate samples were run in which 200 ul of specimen (serum) was added to 100 μl of the combined reagent containing $^{125}$I-labelled antibodies and FITC conjugated antibody and incubated for 2 hours at room temperature. 200 μl of anti-FITC magnetisable solid phase suspension was then added and incubated for 5 minutes, after mixing. The solid phase particles were separated magnetically, the liquid removed by decantation and the particles washed by addition of 1 ml buffer. Following this, the particles were again separated magnetically, the wash liquid removed by decantation and the resultant pellet counted for bound $^{125}$I-labelled antibody. An example dose response curve is shown in FIG. 1. Counts per minute bound are plotted along the vertical axis and micro international units human TSH/ml are plotted along the horizontal axis.

EXAMPLE 2

Assay of TSH

In this assay, selective binding of the reagent (c) to the bound reagent (d) was achieved by using anti-TSH antibody raised in rabbits as reagent (c), bound anti-rabbit antibody as reagent (d) and one type of $^{125}$I-labelled antibody from a different animal species.

Preparation of the starting materials (i) $^{125}$I-labelled anti-TSH monoclonal antibody reagent $^{125}$I-labelled monoclonal antibodies to TSH (from mouse ascites fluid) were prepared as described in Example 1, and diluted to achieve $4 \times 10^6$ counts per minute per ml in a buffer system of sodium phosphate 0.05M, pH 7.4 containing 0.5% (w/v) bovine serum albumin, 0.2% (v/v) normal (non-immune) sheep serum and 0.2% (w/v) sodium azide.

(ii) Polyclonal anti-TSH antibody reagent

Conventional, high titre, polyclonal anti-TSH antiserum, raised in rabbits, was diluted in the same buffer system as used for $^{125}$I-labelled monoclonal antibodies.

(iii) Solid phase reagent comprising anti-rabbit IgG antibody linked to magnetisable cellulose particles Anti-rabbit IgG was a polyclonal antiserum raised in sheep. It was covalently coupled to magnetisable particles in an identical manner to the antiFITC antiserum of Example 1, at a coupling ratio of 2 ml antiserum per gram magnetisable solid phase. The magnetisable particles were diluted to a concentration of 10 mg/ml in a buffer system of sodium phosphate 0.05M, pH 7.4 containing 0.25% (w/v) bovine serum albumin, 0.25% (v/v) Triton X-100 and 0.1% (w/v) sodium azide.

Determination of TSH

Solutions of TSH in normal human serum, calibrated against the 1st International Reference Preparation of human TSH for immunoassay (68/38), were used as standards.

Duplicate samples were run in which 200 μul of specimen (serum) was mixed with 50 μl of $^{125}$I-labelled monoclonal antibodies and incubated for 2 hours at room temperature. 50 μl of rabbit anti-TSH antiserum solution was then added and the mixtures incubated for a further 2 hours at room temperature. Following this, 200 μl of anti-rabbit IgG magnetisable solid phase suspension was added, left for 5 minutes before mixing, then incubated for 15 minutes. The solid phase particles were then separated magnetically, the liquid removed by decantation and the particles washed by addition of 0.5 ml distilled water. The magnetic separation was then repeated, and after decantation, the resultant pellet counted for bound $^{125}$I-labelled antibody. An example dose response curve is shown in FIG. 2. Counts per minute bound are plotted along the vertical axis and micro international units human TSH/ml are plotted along the horizontal axis.

EXAMPLE 3

Assay of TSH

In this assay, selective binding of reagents (c) and (d) was carried out by the same method of Example 1, with Fab' fragments being used in place of intact $^{125}$I-labelled antibody.

Preparation of the starting materials (i) Combined reagent comprising $^{125}$I-labelled Fab' monoclonal antibody fragments and FITC conjugated monoclonal antibody.

F(ab')2 fragments of mouse monoclonal anti-TSH were obtained by incubating 250 μg of thiol activated papain with 5 mg antibody in 1.5 ml of sodium acetate buffer 0.1M, pH 5.5 containing 0.003M EDTA for 18 hours at 37° C. The mixture was purified by chromatography on Sepharose protein A followed by gel filtration on Sephacryl S-200. Monovalent Fab' fragments were prepared by reacting 0.5 mg F(ab')2 in a solution (0.6 ml) of 8-mercaptoethylamine 0.1M in sodium phosphate buffer 0.1M pH 7.4 for 90 minutes at 20° C. followed by purification by gel filtration on Sephacryl S-200.

Fab' fragments were labelled with $^{125}$I in an analogous manner to the intact monoclonal antibodies described in Example 1, giving a product with an average of greater than 1/10 atom $^{125}$I per molecule of Fab'.

The $^{125}$I-labelled Fab' anti-TSH was combined in a single reagent with FITC conjugated monoclonal antibody (prepared as described in Example 1), containing $2 \times 10^6$ counts per minute per ml $^{125}$I-labelled Fab' and 2.5 μg/ml FITC conjugated antibody, in a buffer system of 0.05M sodium phosphate, pH 7.4 containing 0.5% (w/v) bovine serum albumin, 0.2% (w/v) normal (non-immune) sheep serum and 0.2% (w/v) sodium azide.

(ii) Solid phase reagent comprising anti-FITC polyclonal antibody covalently linked to magnetisable cellulose particles.

Prepared in the manner described in Example 1.

Determination of TSH

All other reagents, and the assay protocol for determination of TSH were as described in Example 1. An example dose response curve is shown in FIG. 3. Counts per ten minutes bound are plotted along the vertical axis and micro international units human TSH/ml are plotted along the horizontal axis.

We claim:

1. A method of immunoassay of an antigen having multiple epitopes in a liquid sample which comprises incubating a mixture of:
   (a) the liquid sample,
   (b) labelled antibodies to the antigen under assay,
   (c) a reagent comprising antibodies to the antigen under assay conjugated with a reagent Z, said reagent Z being a hapten or antigenic substance, and,
   (d) an antibody reagent raised to reagent Z which selectively interacts with reagent Z by non-covalent bonding, but which is not directly bindable to either component (a) or component (b) the said reagent (d) being bound to a solid phase support and
   at least said components (b) and (c) comprising monoclonal antibodies;

separating the solids fraction from the liquid fraction, determining the amount of label in one of the said fractions and, therefrom the amount of antigen present in the sample.

2. A method as claimed in claim 1, wherein antibodies (b) and (c) are of a different antibody class or sub-class of the same animal species.

3. A method of immunoassay of an antigen having multiple epitopes in a liquid sample which comprises incubating a mixture of:
(a) the liquid sample,
(b) labelled antibodies to the antigen under assay, in the form of Fab-type fragments,
(c) a reagent comprising intact antibodies or half-molecule fragments, the latter of the same animal species as the fragments of component (b), to the antigen under assay, and
(d) a reagent capable of binding to component (c) by non-covalent bonding, but which is not directly bindable to either component (a) or component (b) comprising an antibody reagent of a different animal species bindable specifically to the Fc part of reagent (c) or Protein A, the said reagent (d) being bound to a solid phase support and at least said components (b) and (c) comprising monoclonal antibodies:

separating the solids fraction from the liquid fraction, determining the amount of label in one of the said fractions and; therefrom; the amount of antigen present in the sample.

4. A method as claimed in claim 1 wherein at least one of the antibody reagents is employed in the form of fragments.

5. A method as claimed in claim 2 wherein at least one of the antibody reagents is employed in the form of fragments.

6. A method as claimed in claim 1 wherein reagent Z is fluorescein isothiocyanate.

7. A kit of reagents for carrying out a method of immunoassay of an antigen having multiple epitopes in a liquid sample comprising containers of (i) labelled monoclonal antibodies to the antigen under assay; (ii) a reagent comprising monoclonal antibodies to the antigen under assay conjugated to a reagent Z, said reagent Z being a hapten or antigenic substance, and (iii) a solid phase support having an antibody reagent raised to reagent Z bound thereto, said bound reagent capable of selectively interacting reagent Z by non-covalent bonding but unable to directly bind to said labelled monoclonal antibodies or the antigen under assay.

8. A kit as claimed in claim 7 wherein reagent Z is fluorescein isothiocyanate.

9. A kit of reagents for carrying out a method of immunoassay of an antigen having multiple epitopes in a liquid sample comprising containers of (i) labelled monoclonal antibodies to the antigen under assay in the form of Fab-type fragments, (ii) a reagent comprising intact monoclonal antibodies or half-molecule fragements, the latter of the same animal species as the fragments of component (i) to the antigen under assay, and (iii) a solid phase support having a reagent bound thereto, said bound reagent comprising an antibody reagent of a different animal species bindable specifically to the Fc part of reagent (ii) by non-covalent bonding but which is not directly bindable to said labelled monoclonal antibodies, or protein A.

* * * * *